United States Patent [19]
Carr et al.

[11] 3,957,986
[45] May 18, 1976

[54] ANTIVIRAL COMPOSITIONS CONTAINING BIS-BASIC ESTERS AND AMIDES OF XANTHENE AND XANTHONE

[75] Inventors: Albert A. Carr; Robert W. Fleming; Arthur D. Sill, all of Cincinnati, Ohio

[73] Assignee: Richardson-Merrell Inc., Wilton, Conn.

[22] Filed: July 2, 1973

[21] Appl. No.: 375,754

Related U.S. Application Data
[62] Division of Ser. No. 162,716, July 14, 1971, Pat. No. 3,859,307.

[52] U.S. Cl. ............................ 424/248; 424/267; 424/274; 424/278; 424/283
[51] Int. Cl.² ........................................ A01N 9/00
[58] Field of Search ........................... 424/283, 293

[56] References Cited
UNITED STATES PATENTS
3,767,674  10/1973  Nabih ........................... 260/328

OTHER PUBLICATIONS
Cecil et al., A Textbook of Medicine, 9th Ed., W. B. Saunders Co., Phila., Pa., 1958, p. 1.

*Primary Examiner*—Richard L. Huff
*Attorney, Agent, or Firm*—George W. Rauchfuss, Jr.; Eugene O. Retter

[57] ABSTRACT

Novel bis-basic esters and amides of xanthene and xanthone of the formula

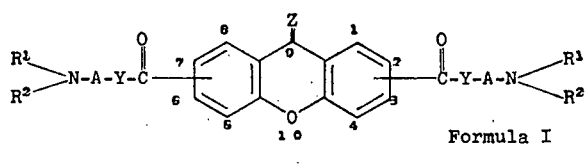

Formula I wherein:
Z is oxygen or $H_2$; each of $R^1$ and $R^2$ is hydrogen, (lower)-alkyl of 1 to 6 carbon atoms, cycloalkyl of 3 to 6 ring carbon atoms, alkenyl of 3 to 6 carbon atoms having the vinyl unsaturation in other than the 1-position of the alkenyl group, or each set of $R^1$ and $R^2$ taken together with the nitrogen atom to which they are attached is pyrrolidino, piperidino, N-(lower)alkylpiperazino, or morpholino;
each A is alkylene of 2 to about 8 carbon atoms and separates its adjacent Y and amino nitrogen by an alkylene chain of at least 2 carbon atoms; and each Y is oxygen, or $>$N—R wherein R is hydrogen or (lower)-alkyl of 1 to 4 carbon atoms;
or a pharmaceutically acceptable acid addition salt thereof. These compounds can be used as pharmaceuticals for preventing or inhibiting a viral infection.

15 Claims, No Drawings

ANTIVIRAL COMPOSITIONS CONTAINING BIS-BASIC ESTERS AND AMIDES OF XANTHENE AND XANTHONE

This is a division of application Ser. No. 162,716, filed July 14, 1971, now U.S. Pat. No. 3,859,307 issued Jan. 7, 1975.

FIELD OF INVENTION

This invention relates to novel bis-basic esters and amides of xanthene and xanthone, their method of preparation and use as antiviral agents.

SUMMARY OF INVENTION

The compounds of this invention include both the base form and pharmaceutically acceptable acid addition salts of the base form wherein the base form can be represented by the formula

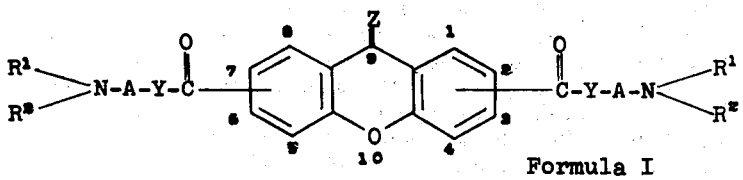

Formula I wherein:
Z is oxygen or $H_2$; each of $R^1$ and $R^2$ is hydrogen, (lower)-alkyl of from 1 to 6 carbon atoms, cycloalkyl of 3 to 6 ring carbon atoms, alkenyl of 3 to 6 carbon atoms having the vinyl unsaturation in other than the 1-position of the alkenyl group, or each set of $R^1$ and $R^2$ taken together with the nitrogen atom to which they are attached is pyrrolidino, piperidino, N-(lower)alkylpiperazino, or morpholino; each A is alkylene of 2 to about 8 carbon atoms and separates its adjacent Y and amino nitrogen by an alkylene chain of at least 2 carbon atoms; and each Y is oxygen, or >N—R wherein R is hydrogen or (lower)alkyl of 1 to 4 carbon atoms, or a pharmaceutically acceptable acid addition salt thereof.

It can be seen from the above Formula I that the basic side chains, that is,

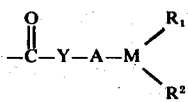

can be linked to the tricyclic ring system by replacement of any of the four hydrogens of presence benzenoid ring to which such group is attached. Thus one of the groups will be in any positions of 1 through 4 of the tricyclic ring system and the other will be in any of the positions 5 through 8. Preferably one of the basic side chains is in the 2-position and the other in the 7-position of the tricyclic ring system.

Each of the alkylene groups as represented by "A" in the above generic Formula I is an alkylene group having from 2 to about 8 carbon atoms which can be straight chained, or branched chained and which separates its adjacent Y from the amino nitrogen by an alkylene chain of at least two carbon atoms. Thus, the Y group and the amino nitrogen are not on the same carbon atom of the alkylene group. Each of the alkylene groups as represented by A can be the same or different. Preferably both of these groups are the same.

Illustrative of alkylene groups as represented by A there can be mentioned: 1,2-ethylene; 1,3-propylene; 1,4-butylene; 1,5-pentylene; 1,6-hexylene; 2-methyl-1,4-butylene; 2-ethyl-1,4-butylene; 3-methyl-1,5-pentylene; 2,2-dimethyl-1,5-pentylene and the like. Preferably, A is alkylene having from 3 to 6 carbon atoms.

Each amino group, i.e.,

of Formula I, can be a primary, secondary or tertiary amino group. Each of $R^1$ and $R^2$ can be hydrogen, (lower)alkyl, cycloalkyl of 3 to 6 ring carbon atoms, alkenyl of 3 to 6 carbon atoms having the vinyl unsaturation in other than the 1-position of the alkenyl group, or each set of $R^1$ and $R^2$ taken together with the nitrogen atom to which they are attached is a saturated monocyclic heterocyclic group.

Illustrative of cycloalkyl groups as represented by each of $R^1$ and $R^2$ there can be mentioned: cyclopropyl; cyclobutyl; cyclopentyl and cyclohexyl. When $R^1$ and $R^2$ represent alkenyl groups, the vinyl unsaturation is in other than the 1-position of said alkenyl group. Illustrative of alkenyl groups as can be represented by each of $R^1$ and $R^2$ there can be mentioned: allyl; 3-butenyl; 4-hexenyl; and the like. Illustrative of heterocyclic groups represented by $R^1$ and $R^2$, together with the nitrogen atom to which they are attached, there can be mentioned various saturated monocyclic heterocyclic groups such as those generally equivalent to di(lower)alkylamino groups in the pharmaceutical arts, e.g., pyrrolidino, piperidino, morpholino, N-(lower)alkylpiperazino such as N-methylpiperazino, N-ethylpiperazino, and the like. Each of the $R^1$ and $R^2$ groups can be the same or different. Preferably all of the $R^1$ and $R^2$ groups are the same. The amino groups are preferably tertiary amino groups such as di(lower)alkylamino, dialkenylamino or each set of $R^1$ and $R^2$ together with the nitrogen to which they are attached is pyrrolidino, piperidino, N-(lower)alkylpiperazino or morpholino.

Each Y group in Formula I can be oxygen or >N—R wherein R is hydrogen or (lower)alkyl of 1 to 4 carbon atoms. Preferably R is hydrogen.

The term (lower)alkyl or (lower)alkoxy as used herein relates to such groups having from 1 to 6 carbon atoms and preferably from 1 to 4 carbon atoms. Illustrative of (lower)-alkyls as can be represented by each of $R^1$ and $R^2$ there can be mentioned straight or branched chain alkyls such as: methyl, ethyl, n-propyl, isopropyl, n-butyl, secondary butyl, teritiary butyl, isoamyl, n-pentyl, n-hexyl, and the like.

It can be seem from the generic Formula I and its description that the compounds of this invention can be (a) xanthene and xanthone esters or (b) xanthene and xanthone amides, which can be illustrated by the following formulas, respectively:

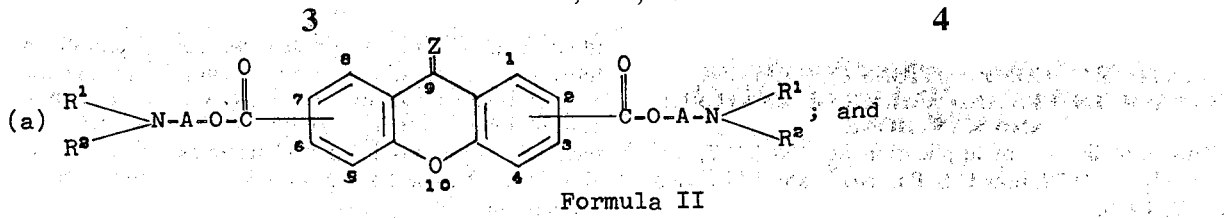

Formula II

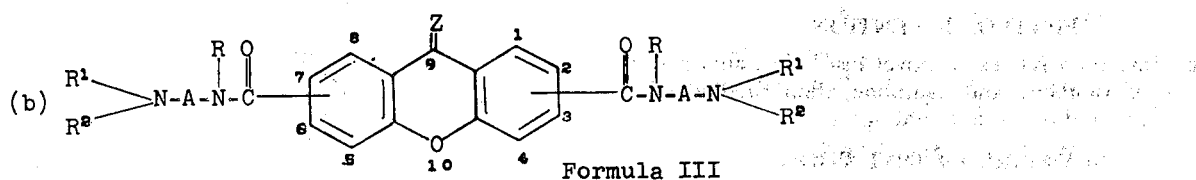

Formula III wherein R, R¹, R², Z and A have the same meaning as that in the description in Formula I.

As examples of compounds of this invention there may be mentioned, for example, bis(3-diethylaminopropyl)-9-oxoxanthene-2,7-dicarboxylate dihydrochloride, bis(3-diethylaminopropyl)xanthene-2,7-dicarboxylate dihydrochloride, bis(3-di-n-butylaminopropyl)-9-oxoxanthene-2,7-dicarboxylate dihydrochloride, bis(3-di-n-butylaminopropyl)xanthene-2,7-dicarboxylate dihydrochloride, N,N'-bis(3-di-n-butylaminopropyl)-9-oxoxanthene-2,7-dicarboxamide, N,N'-bis(3-di-n-butylaminopropyl)xanthene-2,7-dicarboxamide, bis(3-piperidinopropyl)-9-oxoxanthene-2,7-dicarboxylate, bis(3-piperidinopropyl)xanthene-2,7-dicarboxylate, bis(5-dimethylamino-2,2-dimethylpentyl)-9-oxoxanthene-2,7-dicarboxylate, bis(5-dimethylamino-2,2-dimethylpentyl)xanthene-2,7-dicarboxylate, bis(3-dicyclohexylaminopropyl)-9-oxoxanthene-2,7-dicarboxylate, bis(3-allylaminopropyl)xanthene-2,7-dicarboxylate, bis(3-morpholinopropyl)-9-oxoxanthene-2,7-dicarboxylate, N,N'-bis(3pyrrolidinopropyl)-9-oxoxanthene-2,7-dicarboxamide, and N,N'-bis[3-(N-methylpiperazino)propyl]-9-oxoxanthene-2,7-dicarboxamide, N,N'-bis(3-di-n-butylaminopropyl)-N,N'-dimethyl xanthene-2,7-dicarboxamide, N,N'-bis(3-tert-butylaminopropyl)xanthene-2,7-dicarboxamide, bis(3-diethylaminopropyl)xanthene-1,8-dicarboxylate, and bis(3-dibutylaminopropyl)xanthene-4,5-dicarboxylate.

Pharmaceutically acceptable acid addition salts of the base compounds of this invention are those of any suitable inorganic or organic acids. Suitable inorganic acids are, for example, hydrochloric, hydrobromic, sulfuric or phosphoric acids and the like. Suitable organic acids are, for example, carboxylic acids such as acetic, propionic, glycolic, lactic, pyruvic, malonic, succinic, fumaric, malic, tartaric, citric, ascorbic, maleic, hydroxymaleic, benzoic, hydroxybenzoic, phenylacetic, cinnamic, salicylic, 2-phenoxybenzoic and the like, or sulfonic acids such as methane sulfonic, 2-hydroxyethane sulfonic acid and the like. Mono- or di-acid salts may be formed, and the salts can be hydrated or substantially anhydrous.

It has been found that the compounds of this invention are effective for inactivating or inhibiting a broad variety of viruses and can thus be employed as antiviral agents. These compounds are effective for preventing or inhibiting characteristic viral disease symptoms in a host by a wide variety of methods of application and composition. They can be administered for an antiviral effect by means which subject the host, or such host and a virus, to the active ingredients. The host is subjected to the active ingredients by bringing together an active ingredient and host, for example, by applying or contacting the host with such active ingredients or simply administering the active ingredient to the host. This includes subjecting the host to such active ingredient prior to infection with a virus, that is, prophylactic use, as well as subjecting the host to such active ingredient after infection, that is, therapeutic use. Thus, in viable biological material hosts subjected to the active ingredients, the replication of viruses is inhibited when the host is infected before or after being subjected to such ingredients. Also, administration by various routes of the active ingredients to an animal host prior to or after infection with the virus prevents or inhibits viral replication and the development of the various disease conditions characteristic of the particular virus. By the term "infection" we simply mean invasion of the host with a pathogenic virus. By the term "host" we mean viable biological material or intact animals which are capable of inducing the formation of interferon and which can support the replication of a virus. Preferably the host is of animal and particularly warm blooded or mammalian origin. Illustrative of hosts for various viruses there can be mentioned viable biological material such as can be used in the production of vaccines, for example, tissue cultures such as that of kidney, lung, amnion cells, embryos, for example, chick allantoic fluid; and various animals, for example, warm blooded animals such as birds or mammals, including mice, rats, guinea pigs, gerbils, ferrets and the like.

The mode of activity of the active ingredients is not rigorously defined. Inter alia, the active ingredients induce the formation of interferon when a host is subjected to such ingredients. Interferon is a known antiviral substance which is involved with the inhibition of the replication of viruses in the presence of a host cell. Some of the viruses susceptible to replication inhibition by interferon are set forth in Horsfall and Tamm, "Viral and Rickettsial Infections of Man", 4th Edition (1965), J.B. Lippencott Company, pages 328–329.

The compounds of the present invention can be administered to animals such as warm blooded animals and particularly mammals to prevent or inhibit infections of picornavirus, for example, encephalomyocarditis; myxovirus, for example, Influenza $A_2$ (Jap/305); arbovirus, for example, Semliki forest; Herpes virus group, for example, herpes simplex; and poxviruses; for example, Vaccinia IHD. When administered prior to infection, that is, prophylactically, it is preferred that the administration be within 0 to 96 hours prior to infection of the animal with pathogenic virus. When administered therapeutically to inhibit an infection, it is preferred that the administration be within about a day or two after infection with pathogenic virus.

The dosage administered will be dependent upon the virus for which treatment jor prophylaxis is desired, the type of animal involved, its age, health, weight, extent of infection, kind of concurrent treatment, if any, frequency of treatment and the nature of the effect desired. Illustratively, a daily dosage of the active ingredients will generally range from less than about 0.1 to over about 500 mg (milligram) per kg (kilogram) or body weight. Illustratively, dosage levels of the administered active ingredient can be intravenous, 0.1 to about 10 mg/kg; intraperitoneal, 0.1 to about 50 mg/kg; subcutaneous, 0.1 to about 250 mg/kg; oral, 0.1 to about 500 mg/kg and preferably about 1 to about 250 mg/kg; intranasal instillation, 0.1 to about 10 mg/kg; and aerosol, 0.1 to about 10 mg/kg of animal body weight.

The novel compounds, together with conventional pharmaceutical carriers can be employed in unit dosage forms such as solids, for example, tablets or capsules or liquid solutions, suspensions or elixirs for oral administration and injections, or liquid solutions, suspensions, emulsions and the like for parenteral use. The quantity of active ingredient in each dosage will generally differ depending on the type of unit dosage, the type of animal and its weight. Thus, each dosage can contain from less than about 2.0 mg to over 3 grams of active ingredients in a significant quantity of a nontoxic pharmaceutical carrier of the type that can be taken orally, applied topically, bucally or parenterally.

The pharmaceutical carrier can, as previously indicated, be a sterile liquid such as water and oils, with or without the addition of a surfactant. Illustrative of oils there can be mentioned those of petroleum, animal, vegetable or synthetic origin, for example, peanut oil, soybean oil, mineral oil, sesame oil, and the like. In general, water, saline, aqueous dextrose, and related sugar solutions and glycols such as propylene glycol or polyethylene glycol are preferred liquid carriers, particularly for injectable solutions. Sterile injectable solutions such as saline, for example, isotonic saline, will ordinarily contain from about 0.5% to 25% and preferably from about 1 to 10% by weight of the active ingredient in the composition.

As mentioned above, oral administration can be in a suitable suspension or syrup, in which the active ingredient ordinarily will constitute from about 0.5 to 10%, and preferably from about 1% to 5%, by weight. The pharmaceutical carrier in such composition can be a watery vehicle such as an aromatic water, a syrup or a pharmaceutical mucilage; also, a suspending agent for viscosity control such as magnesium aluminum silicate, carboxymethylcellulose or the like as well as a buffer, preservative, etc.

The active ingredients can also be admixed in animal feed or incorporated into the animal's drinking water. For most purposes, an amount of active ingredient will be used to provide from about 0.0001% to 0.1 % by weight of the active ingredient based on the total weight of feed intake. Preferably, from 0.001% to 0.02% by weight will be used. The selection of the particular feed is within the knowledge of the art and will depend, of course, on the animal, the economics, natural materials available, and the nature of the effect desired.

The active ingredients can be admixed in animal feed concentrates, suitable for preparation and sale to farmers or livestock growers for addition to the animal's feedstuffs in appropriate proportion. These concentrates can ordinarily comprise about 0.5% to about 95% by weight of the active ingredient compounded together with a finely divided solid, preferably flours, such as wheat, corn, soya bean and cottonseed. Depending on the recipient animal, the solid adjuvant can be ground cereal, charcoal, fuller's earth, oyster shell and the like. Finely divided attapulgite and bentonite can also be used.

The feed compositions, as well as the feed concentrates, can additionally contain other components of feed concentrates or animal feeds, as will be readily understood. Other particularly important additives include proteins, carbohydrates, fats, vitamins, minerals, antibiotics, etc.

For use as aerosols the active ingredients can be packaged in a pressurized aerosol container together with a gaseous or liquefied propellant, for example, dichlorodifluoromethane, carbon dioxide, nitrogen, propane, etc. with the usual adjuvants such as co-solvents, and wetting agents, as may be necessary or desirable.

Typical surface active agents (kirk and Othmer, Encyclopedia of Chemical Terminology, 1954, Vol. 13, page 513), particularly emulsifying and dispersing agents which can be used in the compositions of this invention are, for example, fatty alcohol sulfates such as sodium lauryl sulfate, aliphatic or aromatic sulfonates, such as sulfonated castor oil, and nonionic types of emulsifying or dispersing agents such as the high molecular weight alkyl polyglycol ethers, such as dodecyl polyglycol ethers containing from about 25 to 75 carbon atoms.

A desirable mode of administration for the compounds (active ingredients) of this invention is parenterally, such as by normally liquid injectable compositions, for example, for intramuscular or subcutaneous administration. In such compositions the quantity of active ingredient can vary from about 0.05% to 20% by weight of the composition and preferably from about 0.1% to 10% by weight. In order to minimize or eliminate irritation at the site of injection, the parenteral compositions can contain a non-ionic surfactant such as those having an HLB (hydrophile-lipophile balance) of about 12 to 17. Such formulations can be solutions, suspensions or emulsions in conventional liquid pharmaceutical carriers, for example, sterile liquids such as water, saline, and aqueous dextrose (glucose) and related sugar solutions. The quantity of surfactant in the formulation can vary from about 5% to 15% by weight of the formulation. The quantity of a compound of this invention, either in the base form or a pharmaceutically acceptable acid addition salt in such formulations, can vary over a broad range, such as that mentioned hereinbefore, that is, 0.05% to 20% by weight of the formulation. Preferably, the active ingredient is in the base form. The remaining component or components of such formulations can be normally liquid pharmaceutical carrier, for example, isotonic aqueous saline, either alone or together with conventional excipients for injectable compositions. The surfactant can be a single surfactant having the above-indicated HLB or a mixture of two or more surfactants wherein such mixture has the indicated HLB. The following surfactants are illustrative of those which can be used in such formulations. (A) Polyoxyethylene derivatives of sorbitan fatty acid esters, such as the TWEEN series of surfactants, for example, TWEEN 80, and the like. The TWEENS are manufactured by Atlas Power Company. (B) High molecular weight adducts of ethylene oxide with a hydrophobic base formed by the condensation of propylene oxide with propylene glycol, for example, PLURONIC F-68 which is manufactured by Wyandotte Chemical Company. The preferred surfactant is Polysorbate 80, U.S.P., a polyoxyethylene sorbitan monooleate.

The compounds of this invention can be prepared by a variety of procedures including the following:

1.

A. The reaction of a xanthene or xanthone dicarboxylic acid or a reactive derivative thereof such as an acid halide, azolide, or ester of the formula

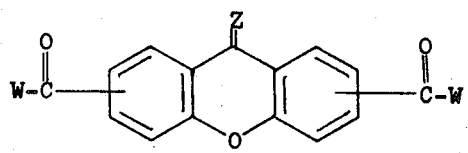

wherein Z is oxygen or H₂, W is hydroxy, halogen such as chlorine or bromine, azolide, or a lower alkoxy such as methoxy or ethoxy, with an aminoalkanol or aminoalkylamine of the formula

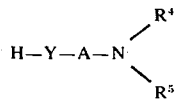

wherein Y is oxygen or >N—R wherein R is hydrogen or (lower)alkyl of 1 to 4 carbon atoms, A is alkylene of 2 to about 8 carbon atoms, either straight chain or branched, and each R⁴ and R⁵ is (lower)alkyl of 1 to 6 carbon atoms, cycloalkyl of 3 to 6 ring carbon atoms, or alkenyl of 3 to 6 carbon atoms having the vinyl unsaturation in other than the 1-position of the alkenyl group, or together with the nitrogen to which they are attached form a heterocyclic group such as those generally equivalent to a di(lower)alkylamino group in the pharmaceutical arts.

B. The esterification can be achieved by allowing the xanthene or xanthone dicarboxylic acid, where W in the above formula is hydroxy, to react with the appropriate aminoalkanol in an inert solvent in the presence of a catalyst and employing general methods for removing water from the reaction site. Preferred solvents are chloroform, isopropanol, dioxane, toluene and the like. The reaction may be catalyzed by the use of mineral acids including hydrochloric, sulfuric or certain organic acids such as p-toluenesulfonic acid. Methods whereby water can be removed from the reaction include the use of water scavengers such as the carbodiimides or by the azeotropic removal of water. The reaction will proceed at temperatures ranging from 100°–250°C. over a period of 6 to 72 hours depending upon the solvent and catalyst.

C. Preferably, the esterification can be achieved by allowing the acid halide, where W in the above formula is halogen, to react with the appropriate aminoalkanol. The esters of this invention can be produced in a variety of inert solvents over a wide range of temperatures and reaction time. The solvents of choice include methylene chloride, chloroform, dioxane, tetrahydrofuran, and the aromatic solvents such as benzene and toluene. In chloroform, the reaction is generally complete within one hour at a temperature of from 20°C. to the reflux temperature of the solvent, although the reaction time can range from 15 minutes to 3 days. In like manner, the amides of this invention can be prepared by allowing the xanthene or xanthone diacid halide to react with the appropriate aminoalkylamine. The preferred reaction conditions are those which employ chloroform as the solvent and heating at the reflux temperature of said solvent for 2–18 hours.

D. The compounds of this invention may also be produced by a transesterification reaction in which a (lower)alkoxy ester of the xanthene or xanthone dicarboxylic acid, where W, for example, is methoxy or ethoxy in the above formula, is caused to react with the appropriate aminoalkanol under suitable conditions. This type of reaction is catalyzed by alkaline or acid catalysts and is reversible. The compounds of this invention may be produced by causing the equilibrium to be shifted by removing the lower alkanol component or by employing a large excess of the aminoalkanol. Preferably, the reaction is carried out by removing the lower alkanol component with the use of an alkaline catalyst. The lower alkanol may be removed by direct distillation or distillation with a suitable solvent. Suitable alkaline catalysts are alkali metals, sodium or potassium; alkali lower alkoxides, such as sodium methoxide or sodium ethoxide; alkali amides such as lithium or sodium amide; etc. Suitable solvents are those forming an azeotropic distillation mixture with the lower alkanol, for example, benzene or toluene, or a solvent which boils sufficiently higher than the alkanol to permit removal of the alkanol by distillation at a temperature below that of the boiling range of the solvent. The amides of this invention may also be produced by allowing the lower alkoxy ester of the xanthene or xanthone dicarboxylic acid to react with the appropriate aminoalkylamine under the conditions as for the esters.

E. The compounds of this invention may also be produced by reacting the xanthene or xanthone dicarboxylic azolide with a diamine or a tertiary aminoalcohol and a catalytic amount of an alkoxide at temperatures of from 25° to 175°C. with or without an aprotic solvent for 1 to 24 hours. As representative of typical azolides which may be used are imidazolides, 1,2,3-triazolides and the like.

2. The esters of this invention can be produced by allowing the xanthene or xanthone dicarboxylic acid, or an activated salt thereof, to react with an aminoalkyl halide in a suitable organic solvent such as chloroform or isopropanol. The aminoalkyl portion of the reactant is the same as in 1A, above. The reaction conditions can vary from 6 hours to 72 hours over a temperature range of from room temperature to the reflux temperature of the solvent employed in the presence or absence of an activating moiety such as inorganic cations including sodium and silver or organic activators such as benzyltrimethylammonium chloride. These activators may be present in stoichiometric amounts or catalytic quantities. Since these activators considerably reduce the reaction time, the preferred conditions are to use a catalytic amount of benzyltrimethylammonium chloride and allow the reaction to proceed for 6–18 hours at the reflux temperature of isopropanol.

3. The compounds of this invention can be prepared by allowing a xanthene or xanthone ω-haloalkyl diester or diamide, prepared by general methods, of the formula:

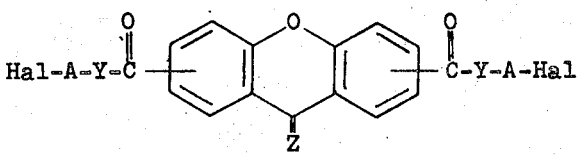

wherein Z, Y and A are as previously defined and Hal is chlorine, bromine or iodine to react with an amine of the formula:

wherein $R^6$ and $R^7$ are (lower)alkyl, or together with the nitrogen to which they are attached form a heterocyclic group such as that generally equivalent to a dialkylamino group. The xanthene or xanthone ω-haloalkyl diester or diamide may be prepared by the reaction of a xanthene or xanthone dicarbonyl chloride with an ω-haloalkanol or an ω-haloalkylamine in a suitable solvent to give the respective products. The preferred halogen in the above formula is bromine or iodine. The reaction is conducted in the presence of stoichiometric amounts of a material which will effectively remove the acid generated in the course of the reaction. Suitable acid binding reagents are anhydrous sodium or potassium carbonate, potassium bicarbonate or extra equivalents of the amine. The solvents of choice are non-protonic organic liquids such as toluene, chloroform, diethyl ether and dioxane. The preferred conditions are those in which components are allowed to react in ethanol at 50° to 150°C. for 3 hours to 72 hours in the presence of potassium iodide.

4. The secondary or primary amino derivatives of the compounds of this invention can be prepared by the various procedures under 1 above, if the amino group of the aminoalkanol is suitably blocked to reactivity by formation of a salt or, preferably, by substituting it with a readily removable blocking group such as trifluoroacetyl, carbobenzoxy or the like, followed by removal of the blocking group with a suitable technique such as mild acid hydrolysis or catalytic reduction.

5. The primary amino derivatives of the compounds of this invention where $R^1$ and $R^2$ are hydrogen may be prepared by converting the corresponding diacids into cyanoalkyl de-derivatives of the formula

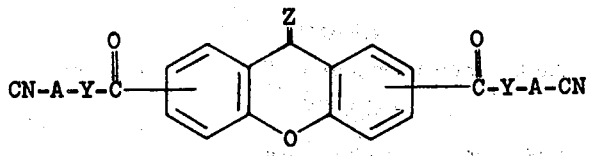

wherein Z, Y and A are as previously defined, and reducing these cyanoalkyl derivatives to primary amine derivatives, such as, by hydrogenation over a platinum oxide or Raney nickel catalyst at 25° to 75°C. for 3 to 72 hours with a solvent such as ethanol or acetic acid, at a hydrogen pressure of about 60 psi or lower. Ammonia may be used with non-acidic solvents to suppress the formation of secondary or tertiary amine by-products.

6. Other compounds of Formula I wherein Z is oxygen may be prepared by oxidation of the corresponding xanthene compounds. The oxidation reaction may be carried out, for example, by air oxidation in pyridine solution containing a catalytic amount of Triton B (tetramethylammonium hydroxide) for a period of from 15 minutes to 12 hours.

7. Other compounds of Formula I wherein Z is $H_2$ may be prepared by reduction of the corresponding xanthone compounds. The reduction reaction may be carried out, for example, by hydrogenation of the xanthone compounds in the presence of a palladium catalyst.

The intermediate xanthene and xanthone dicarboxylic acid compounds are generally known; see, for example, J. Pharm. Soc. Japan, 53, 462 (1933), Ber. 44, 852 (1911), Beil. 18, 499, and Chemical Abstracts, 37, 374[1].

EXAMPLES

The following examples are illustrative of the compounds of this invention and their preparation.

EXAMPLE 1

Bis(3-diethylaminopropyl)-9-oxoxanthene-2,7-dicarboxylate dihydrochloride

To 14.2 g (0.05 mole) of xanthone-2,7-dicarboxylic acid was added 150 ml. (2.1 moles) of thionyl chloride and 100 ml of dry tetrahydrofuran. The resulting solution was refluxed for three hours and then the solvent and excess thionyl chloride removed at reduced pressure on a steam bath. The residue was dissolved in 500 ml of dry methylene chloride, treated with activated charcoal and filtered. To the filtrate, containing xanthone-2,7-dicarboxylic acid chloride, was added 17 g (0.13 mole) of 3-diethylamino-1-propanol. The resulting mixture was refluxed 1.5 hours and let stand for three days. The solvent was removed and the residue dissolved in dilute hydrochloric acid and washed with methylene chloride. The aqueous layer was made basic with 15% sodium carbonate solution and extracted with methylene chloride. This solution was washed with dilute sodium carbonate solution and water and then dried over anhydrous magnesium sulfate. Upon filtering, the solvent was removed under reduced pressure and the residue dissolved in isopropanol and converted to the dihydrochloride with ethanolic-HCl. The product was precipitated with diethyl ether, filtered and purified from isopropanolmethanol to give 8.7 g (29.8%) of bis-(3-diethylaminopropyl)-9-oxoxanthene-2,7-dicarboxylate dihydrochloride. M.P. 269.5°–270.5°C.

EXAMPLE 2

Bis(3-di-n-butylaminopropyl)-9-oxoxanthene-2,7-dicarboxylate dihydrochloride

Following the procedure of Example 1, 28.4 g (0.1 mole) of xanthone-2,7-dicarboxylic acid was converted to the corresponding diacid chloride and reacted with 38 g. (0.20 mole) 3-di-n-butylamino-1-propanol to give 9.0 g (12.9%) of the dihydrochloride of bis(3-di-n-butylaminopropyl)-9-oxoxanthene-2,7-dicarboxylate. M.P. 222.5°–223.5°C. from isopropanol.

EXAMPLE 3

N,N'-Bis(3-di-n-butylaminopropyl)-9-oxoxanthene-2,7-dicarboxamide

To 28.4 g (0.1 mole) of xanthone-2,7-dicarboxylic acid was added 200 ml (2.8 moles) of thionylchloride and 200 ml of dry tetrahydrofuran. The resulting solution was refluxed two hours and the solvent and excess thionyl chloride removed at reduced pressure at less than 60°C. Dry benzene was added and the resulting solution was concentrated to about half volume to remove the last traces of thionyl chloride and then concentrated to a solid residue. This material was dissolved in methylene chloride and treated by the slow addition of 37.2 g (0.2 mole) of N,N-di-n-butyl propylenediamine. After stirring for five minutes, the solvent was removed at reduced pressure. The resulting material was partitioned between chloroform and 5% sodium hydroxide solution. The separated chloroform layer and two chloroform washings of the aqueous layer were combined, washed with water, dried (anhydrous magnesium sulfate) and concentrated at reduced pressure to a solid residue. This material was recrystallized from diethyl ether to give 17 g (27.4%) of N,N'-bis(3-di-n-butylaminopropyl)-9-oxoxanthene-2,7-dicarboxamide. M.P. 89°–92° C.

EXAMPLE 4

Bis(3-di-n-butylaminopropyl)xanthene-2,7-dicarboxylate dihydrochloride

To 17.4 g (0.06 mole) of xanthene-2,7-dicarboxylic acid was added 100 ml (1.4 moles) of thionyl chloride and 4 drops of pyridine. The resulting solution was refluxed for four hours and solvent and excess thionyl chloride were removed. The intermediate diacid chloride in benzene-methylene chloride was reacted with 24 g (0.13 mole) of 3-di-n-butylamino-1-propanol by refluxing for three hours. Most of the solvent was removed and the residue allowed to stand for two days. The residue was diluted with methylene chloride and 10% hydrochloric acid. The organic layer and two methylene chloride washings of the aqueous layer were combined and dried over anhydrous magnesium sulfate. The solution was filtered and concentrated at reduced pressure to a solid residue. This was purified from isopropanol to give 12.9 g (29.6%) of bis(3-di-n-butylaminopropyl)xanthene-2,7-dicarboxylate dihydrochloride. M.P. 187.5°–190°C.

EXAMPLE 5

N,N'-Bis(3-di-n-butylaminopropyl)xanthene-2,7-dicarboxamide

An alcoholic solution of N,N'-bis(3-di-n-butylaminopropyl)-9-oxoxanthene-2,7-dicarboxamide, prepared in Example 3, can be used with a palladium catalyst to effect a hydrogenation to give N,N'-bis(3-di-n-butylaminopropyl)xanthen-2,7-dicarboxamide.

EXAMPLE 6

Following the procedure of Example 1, only substituting for 3-diethylaminopropanol the appropriate molar equivalent of 3-piperidinopropanol, 5-dimethylamino-2,2-dimethylpentanol, 3-dicyclohexylaminopropanol and 3-morpholinopropanol the following compounds are prepared, respectively:
bis(3-piperidinopropyl)-9-oxoxanthene-2,7-dicarboxylate dihydrochloride,
bis(5-dimethylamino-2,2-dimethylpentyl)-9-oxoxanthene-2,7-dicarboxylate dihyrochloride,
bis(3-dicyclohexylaminopropyl)-9-oxoxanthene-2,7-dicarboxylate dihydrochloride, and
bis(3-morpholinopropyl)-9-oxoxanthene-2,7-dicarboxylate dihydrochloride.

These compounds are converted to the corresponding xanthene dicarboxylate compounds by reducing these oxoxanthene compounds in the presnece of a palladium catalyst.

EXAMPLE 7

Following the procedure of Example 3, only substituting for N,N-di-n-butylpropylene diamine the appropriate molar equivalents of 3-pyrrolidinopropylamine and 3-(N-methylpiperazino)propylamine, the following compounds are prepared, respectively:
N,N'-bis (3-pyrrolidinopropyl)-9-oxoxanthene-2,7-dicarboxamide, and N,N'-bis[3-(N-metylpiperazino)-propyl]-9-oxoxanthene-2,7-dicarboxamide.

These compounds are converted to the corresponding xanthene dicarboxamide compounds by reducing these oxoxanthene carboxamides in the presence of a palladium catalyst.

EXAMPLE 8

An illustrative composition for hard gelatin capsules is as follows:

| | Per Capsule |
|---|---|
| (a) Bis(3-diethylaminopropyl)-9-oxoxanthene-2,7-dicarboxylate dihydrochloride | 200 mg. |
| (b) Talc | 35 mg. |

The formulation is prepared by passing the dry powders of (a) and (b) through a fine mesh screen and mixing them well. The powder is then filled into N. 0 hard gelatin capsules at a net fill of 235 mg. per capsule.

EXAMPLE 9

An illustrative composition for tablets is as follows:

| | Per Tablet |
|---|---|
| (a) Bis(3-diethylaminopropyl)-9-oxoxanthene-2,7-dicarboxylate dihydrochloride | 100 mg. |
| (b) Wheat starch | 15 mg. |
| (c) Lactose | 33.5 mg. |
| (d) Magnesium stearate | 1.5 mg. |

Preparation:
A granulation obtained upon mixing lactose with the starch and granulated starch paste is dried, screened and mixed with the active ingredient and magnesium stearate. The mixture is compressed in tablets weighing 150 mg. each.

EXAMPLE 10

An illustrative composition for pills is as follows:

| | Per Pill |
|---|---|
| (a) Bis(3-diethylaminopropyl)-9-oxoxanthene-2,7-dicarboxylate dihydrochloride | 100 mg. |
| (b) Starch, corn | 90 mg. |
| (c) Liquid glucose | 10 mg. |

The pills are prepared by blending the active ingredient and starch and then adding the liquid glucose with thorough kneading to form a plalstic mass. The pills are then cut and formed from the plastic pill mass.

EXAMPLE 11

A 2% weight per volume syrup of bis(3-diethylaminopropyl)-9-oxoxanthene-2,7-dicarboxylate dihydrochloride can be prepared by the usual pharmaceutical techniques according to the following formula:

| | Grams |
|---|---|
| (a) Finely divided bis(3-diethylaminopropyl)-9-oxoxanthene-2,7-dicarboxylate dihydrochloride | 2.0 |
| (b) Sucrose | 33.3 |
| (c) Chloroform | 0.25 |
| (d) Sodium benzoate | 0.4 |

-continued (e) Methyl p-hydroxybenzoate 0.02
(f) Vanillin 0.04
(g) Glycerol 1.5
(h) Purified water to 100.0 ml.

EXAMPLE 12

Bis(3-diethylaminopropyl)-9-oxoxanthene-2,7-dicarboxylate dihydrochloride is mixed with soybean meal toprepared an animal feed concentrate containing 10 grams of said oxoxanthene compound per pound of the medicated feed. This can subsequently be diluted with a mixed grain ration to give a medicated feed containing 50 milligrams of the oxoxanthene per pound of the medicated feed.

EXAMPLE 13

The following formulation is illustrative of a dusting powder:

| | Per Kilogram |
|---|---|
| (a) Bis(3-diethylaminopropyl)-9-oxoxanthene-2,7-dicarboxylate dihydrochloride | 20 grams |
| (b) Silica aerogel | 980 grams |

The dusting powder is prepared by intmately admixing the ingredients. The mixture is then packaged in dispensing containers.

EXAMPLE 14

An illustrative composition for a parenteral injection is the following aqueous emulsion.

| Each ml. contains Ingredients | | Amount |
|---|---|---|
| 50 mg. | Bis(3-diethylaminopropyl)-9-oxoxanthene-2,7-dicarboxylate dihydrochloride | 1.000 g. |
| 100 mg. | Polyoxyethylene sorbitan monooleate | 2.000 g. |
| 0.0064 gm. | Sodium chloride | 0.128 g. |
| | Water for injection, q.s. | 20.000 ml. |

The composition of Example 14 is prepared by dissolving 0.64 g. of sodium chloride in 100 ml. of water for injection; mixing the polyoxyethylene sorbitan monooleate with the oxoxanthene, adding a sufficient solution of the sodium chloride in water to the active ingredient and polyoxyethylene sorbitan monooleate to make 20 ml, shaking the mixture, and then autoclaving it for 20 minutes, at 110°C. at 15 p.s.i.g. steam pressure. The composition can be dispensed in a single ampule for multiple dosage or in 10 or 20 ampules for single dosages.

We claim:

1. A pharmaceutical composition in unit dosage form comprising a significant quantity of a pharmaceutical carrier and from about 2.0 milligrams to 3 grams of a compound of the formula

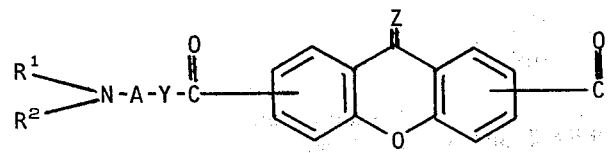

wherein:

Z is oxygen or $H_2$; each of $R^1$ and $R^2$ is hydrogen, (lower)-alkyl, cycloalkyl of 3 to 6 ring carbon atoms, alkenyl of 3 to 6 carbon atoms having the vinyl unsaturation in other than the 1-position of the alkenyl group, or each set of $R^1$ and $R^2$ taken together with the nitrogen atom to which they are attached is pyrrolidino, piperidino, N-(lower)-alkylpiperazino, or morpholino;

each A is alkylene of 2 to about 8 carbon atoms and separates its adjacent Y and amino nitrogen by an alkylene chain of at least 2 carbon atoms; each Y is oxygen, or N-R wherein R is hydrogen or (lower)-alkyl of 1 to 4 carbon atoms;

or a pharmaceutically acceptable acid addition salt thereof.

2. The pharmaceutical composition of claim 1 wherein in the formula of the compound each A is alkylene of 2 to 6 carbon atoms; and each of the

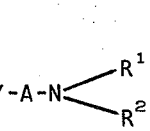

groups is a tertiary amino group selected from di(-lower)alkylamino, dialkenylamino, or each set of $R^1$ and $R^2$ together with the nitrogen to which they are attached is pyrrolidino, piperidino, N-(lower)alkylpiperazino or morpholino.

3. The composition of claim 1 wherein the compound is bis(3-diethylaminopropyl)-9-oxoxanthene-2,7-dicarboxylate or a pharmaceutically acceptable acid addition salt thereof.

4. The composition of claim 1 wherein the compound has the formula

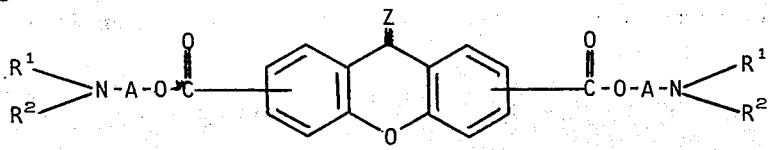

wherein the substitutent groups

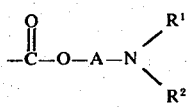

are at the 2- and 7-positions and

Z is oxygen or $H_2$; each of $R^1$ and $R^2$ is hydrogen, (lower)-alkyl, cycloalkyl of 3 to 6 ring carbon atoms, alkenyl of 3 to 6 carbon atoms having the vinyl unsaturation in other than the 1-position of the alkenyl group, or each set of $R^1$ and $R^2$ taken together with the nitrogen atom to which they are attached is pyrrolidino, piperidino, N-(lower)-alkylpiperazino, or morpholino; and each A is alkylene of 2 to about 8 carbon atoms and separates its adjacent O and amino nitrogen by an alkylene chain of at least 2 carbon atoms;

or a pharmaceutically acceptable acid addition salt thereof.

5. The composition of claim 4 wherein in the formula of the compound each of $R^1$ and $R^2$ is (lower)alkyl of 1 to 4 carbon atoms.

6. The composition of claim 1 wherein the compound has the formula

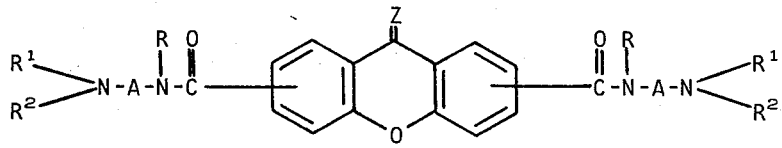

wherein the substituent groups

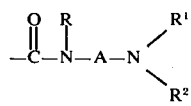

are the 2- and 7-positions and wherein:

Z is oxygen or $H_2$; each of $R^1$ and $R^2$ is hydrogen, (lower)-alkyl, cycloalkyl of 3 to 6 ring carbon atoms, alkenyl of 3 to 6 carbon atoms having the vinyl unsaturation in other than the 1-position of the alkenyl group, or each set of $R^1$ and $R^2$ taken together with the nitrogen atom to which they are attached is pyrrolidino, piperidino, N-(lower)-alkylpiperazino, or morpholino; and each A is alkylene of 2 to about 8 carbon atoms and separates its adjacent amide nitrogen and amino nitrogen by an alkylene chain of at least 2 carbon atoms; each R is hydrogen or (lower)alkyl;

or a pharmaceutically acceptable acid addition salt thereof.

7. The composition of claim 6 wherein in the formula of the compound each of $R^1$ and $R^2$ is (lower)alkyl of 1 to 4 carbon atoms.

8. A method for preventing or inhibiting a viral infection susceptible to replication inhibition by interferon induction which comprises administering to a warm blooded animal, having cells susceptible to invasion by pathogenic viral agents within an antivirally effective time period, an antivirally effective quantity of a compound of the formula

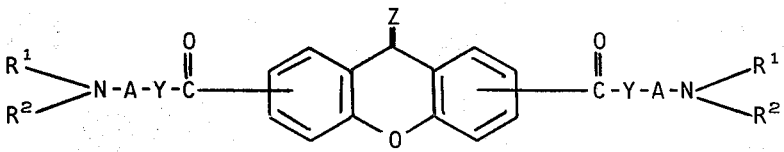

wherein:

Z is oxygen or $H_2$; each of $R^1$ and $R^2$ is hydrogen, (lower)-alkyl, cycloalkyl of 3 to 6 ring carbon atoms, alkenyl of 3 to 6 carbon atoms having the vinyl unsaturation in other than the 1-position of the alkenyl group, or each set of $R^1$ and $R^2$ taken together with the nitrogen atom to which they are attached is pyrrolidino, piperidino, N-(lower)-alkylpiperazino, or morpholino;

each A is alkylene of 2 to about 8 carbon atoms and separates its adjacent Y and amino nitrogen by an alkylene chain of at least 2 carbon atoms;

each Y is oxygen, or N—R wherein R is hydrogen or (lower)-alkyl of 1 to 4 carbon atoms;

or a pharmaceutically acceptable acid addition salt thereof.

9. The method of claim 8 wherein the antivirally effective quantity of the compound amdinistered is from 0.1 to 500 milligrams per kilogram of animal body weight.

10. The method of claim 9 wherein in the formula of the compound administered each A is alkylene of 2 to 6 carbon atoms; and each of the

groups is a tertiary amino group selected from di(-lower)alkylamino dialkenylamino, or each set of $R^1$ and $R^2$ together with the nitrogen to which they are attached is pyrrolidino, piperidino, N-(lower)alkylpiperazino or morpholino.

11. The metod of claim 9 wherein the compound administered is bis(3-diethylaminopropyl)-9-oxoxanthene-2,7-dicarboxylate or a pharmaceutically acceptable acid addition salt thereof.

12. The method of claim 9 wherein the compound administered has the formula

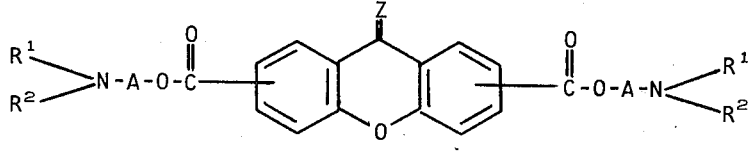

wherein the substituent groups

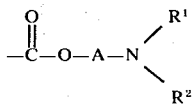

are at the 2- and 7-positions and

Z is oxygen or $H_2$; each of $R^1$ and $R^2$ is hydrogen, (lower)-alkyl, cycloalkyl of 3 to 6 ring carbon atoms, alkenyl of 3 to 6 carbon atoms having the vinyl unsaturation in other than the 1-position of the alkenyl group, or each set of $R^1$ and $R^2$ taken together with the nitrogen atom to which they are attached is pyrrolidino, piperidino, N-(lower)-alkylpiperazino, or morpholino; and each A is alkylene of 2 to about 8 carbon atoms and separates its adjacent O and amino nitrogen by alkylene chain of at least 2 carbon atoms;

or a pharmaceutically acceptable acid addition salt thereof.

13. The method of claim 12 wherein each of $R^1$ and $R^2$ is (lower)alkyl of 1 to 4 carbon atoms.

14. The method of claim 9 wherein the compound administered has the formula

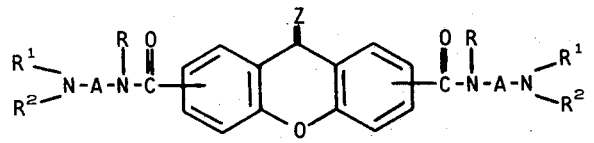

wherein the substituent groups

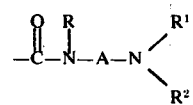

are at the 2- and 7-positions and wherein:

Z is oxygen or $H_2$; each of $R^1$ and $R^2$ is hydrogen, (lower)-alkyl, cycloalkyl of 3 to 6 ring carbon atoms, alkenyl of 3 to 6 carbon atoms having the vinyl unsaturation in other than the 1-position of the alkenyl group, or each set of $R^1$ and $R^2$ taken together with the nitrogen atom to which they are attached is pyrrolidino, piperidino, N-(lower)-alkylpiperazino, or morpholino; and each A is alkylene of 2 to about 8 carbon atoms and separates its adjacent amide nitrogen and amino nitrogen by an alkylene chain of at least 2 carbon atoms; each R is hydrogen or (lower)alkyl;

or a pharmaceutically acceptable acid addition salt thereof.

15. The method of claim 14 wherein each of $R^1$ and $R^2$ is (lower)alkyl of 1 to 4 carbon atoms.

* * * * *

UNITED STATES PATENT AND TRADEMARK OFFICE
CERTIFICATE OF CORRECTION

PATENT NO. : 3,957,986  
DATED : May 18, 1976  
INVENTOR(S) : Albert A. Carr, Robert W. Fleming and Arthur D. Sill It is certified that error appears in the above-identified patent and that said Letters Patent are hereby corrected as shown below:

Page 1 of 2

Column 1, lines 46-52, " $-\overset{O}{\underset{\|}{C}}-Y-A-M\overset{R_1}{\underset{R^2}{\diagdown}}$ " should read " $-\overset{O}{\underset{\|}{C}}-Y-A-N\overset{R^1}{\underset{R^2}{\diagdown}}$ "; line 54, "of presence benzenoid" should read "of the benzenoid". Column 4, line 28, ' term 37 infection" ' should read ' term "infection" '; line 67, "treatment jor" should read "treatment or". Column 5, line 2, "(kilogram) or" should read "(kilogram) of". Column 11, line 44, "butylaminopropyl)xanthen-2,7-" should read "butylaminopropyl)-xanthene-2,7-"; line 63, "in the presnece" should read "in the presence". Column 12, line 5, "[3-(N-metylpiperazino)" should read "[3-(N-methylpiperazino)"; line 23, "filled into N.O" should read "filled into No. O"; line 54, "plalstic" should read "plastic". Column 13, line 11, "toprepared" should read "to prepare"; lines 34-36, "
| Each ml contains | Ingredients | Amount |
|---|---|---|
| 50 mg | Bis(3-diethyl...... | |

" and should read

"
| Each ml contains | Ingredients | Amount |
|---|---|---|
| 50 mg | Bis(3-diethyl...... | |

"

Column 15, line 31, "are the 2- and" should read "are at the 2- and"; claim 7, line 46, "The composition of claim 6" should read "The composition of claim 4". Column 16, line 26,

UNITED STATES PATENT AND TRADEMARK OFFICE
CERTIFICATE OF CORRECTION

PATENT NO. : 3,957,986

DATED : May 18, 1976

INVENTOR(S) : Albert A. Carr, Robert W. Fleming and Arthur D. Sill

It is certified that error appears in the above-identified patent and that said Letters Patent are hereby corrected as shown below:

"amdinistered" should read "administered"; line 43, "metod" should read "method".

Signed and Sealed this

Seventh Day of March 1978

[SEAL]

Attest:

RUTH C. MASON  
Attesting Officer

LUTRELLE F. PARKER  
Acting Commissioner of Patents and Trademarks